United States Patent [19]

Gross

[11] Patent Number: 4,924,714
[45] Date of Patent: May 15, 1990

[54] APPARATUS FOR THE TRANSPORT OF PARTIALLY TEMPERATURE-CONTROLLED TEST MATERIAL IN STRIP FORM

[75] Inventor: Jürgen Gross, Hofheim am Taunus, Fed. Rep. of Germany

[73] Assignee: Hoechst Aktiengesellschaft, Frankfurt am Main, Fed. Rep. of Germany

[21] Appl. No.: 423,579

[22] Filed: Oct. 11, 1989

Related U.S. Application Data

[63] Continuation of Ser. No. 187,008, Apr. 27, 1988, abandoned.

[30] Foreign Application Priority Data

Apr. 29, 1987 [DE] Fed. Rep. of Germany ....... 3714294

[51] Int. Cl.⁵ .............................................. G01N 1/00
[52] U.S. Cl. .................................. 73/863.11; 422/66; 436/44
[58] Field of Search .............................. 422/63, 65-67, 422/73, 66; 436/44; 73/432.1, 64.1, 863.11; 219/388, 388.5, 405, 411, 354

[56] References Cited

U.S. PATENT DOCUMENTS

| | | | |
|---|---|---|---|
| 2,674,809 | 4/1954 | Meienhofer | 219/388 |
| 3,778,964 | 12/1973 | Rowland | 219/388 |
| 3,790,346 | 2/1974 | Ritchie | 422/73 |
| 3,929,920 | 12/1975 | Komo et al. | 422/225 |
| 4,039,287 | 8/1977 | Moran | 422/65 |
| 4,170,073 | 10/1979 | Ignatowicz | 219/388 |
| 4,189,631 | 2/1980 | Baker et al. | 219/385 |
| 4,325,910 | 4/1982 | Jordan | 422/63 |
| 4,453,406 | 6/1984 | Spitzer . | |
| 4,486,172 | 12/1984 | Dunning | 219/388 |
| 4,554,437 | 11/1985 | Wagner et al. | 219/354 |
| 4,680,450 | 7/1987 | Thorson et al. | 219/343 |
| 4,687,895 | 8/1987 | Citre et al. | 219/388 |

FOREIGN PATENT DOCUMENTS 0054849 6/1982 Fed. Rep. of Germany .

Primary Examiner—Robert R. Raevis
Attorney, Agent, or Firm—Finnegan, Henderson, Farabow, Garrett and Dunner

[57] ABSTRACT

An apparatus for transporting test material in strip form underneath a measuring device, the test material having various test zones along the length of the strip, the apparatus comprising conveyor means for transporting the test material; a retaining device disposed above the conveyor means at an angle transverse to the direction of movement of the conveyor means; and at least one heating device disposed on the retaining device for selectively heating individual test zones on the test material as the test material is transported by the conveyor means.

4 Claims, 1 Drawing Sheet

APPARATUS FOR THE TRANSPORT OF PARTIALLY TEMPERATURE-CONTROLLED TEST MATERIAL IN STRIP FORM

This application is a continuation of application Ser. No. 07/187,008, filed Apr. 27, 1988, now abandoned.

BACKGROUND OF THE INVENTION

1. Field of the Invention

The subject-matter of the invention is an apparatus for the transport of partially temperature-controlled test material in strip form underneath a measuring device by means of a conveyor belt for receiving the material to be measured.

2. Description of the Related Art

It is known to examine body fluids by means of test strips for their concentration, for example of sugar, bilirubin, urobilinogen, pH, etc. The test strips have a plurality of test zones having specific analytical reagents which, with the substances contained in the body fluid, induce quite specific colorations. It is further known to analyse such test strips photometrically, in particular remission-photometrically by means of multi-channel photometers. Such multi-channel photometers have an apparatus for the feeding of the test strips. According to European Patent Specification No. 0,054,849, this consists of a conveyor belt which is led underneath the measuring head of the multi-channel photometer. On the conveyor belt there are test strips which are laid on the conveyor belt transversely to its direction of movement and are transported step by step to the measuring head. It has been found in this context that the incubation times of the individual test zones are different. While, at a chosen transport rate, a number of test zones have already virtually reached the end of their reaction by the time of the measurement, and thus can no longer indicate a change in concentration, for other test zones this time is not sufficient, in particular if concentrations are small.

SUMMARY OF THE INVENTION

The invention is consequently based on the object of creating an apparatus which allows the reaction times of the individual test zones to be matched to one another or the detection sensitivity of individual test zones to be increased.

The object is achieved by a transport apparatus wherein a retaining device is provided above the apparatus and transverse to the direction of movement of the conveyor belt and on which at least one heating device is displaceably arranged.

The heating device may consist of a plurality of heat radiators which are arranged one behind the other in the direction of movement of the conveyor belt and are provided with a temperature controller, or of band heaters with varying distance from the conveyor belt. Depending on the number of test zones, one to nine heating devices may be arranged on the retaining device perpendicular to the direction of movement of the conveyor belt.

Among the advantages to be seen in the invention are that the reaction can be selectively accelerated by irradiation of the test zones. As a result, not only the sensitivity of the measurement can be increased by a factor of 3 to 4, but so too can the throughput of strips in the measuring apparatus.

BRIEF DESCRIPTION OF THE DRAWINGS

The invention is explained in more detail below with reference to figures illustrating just one embodiment and in which.

DESCRIPTION OF THE PREFERRED EMBODIMENT

Figure 2:
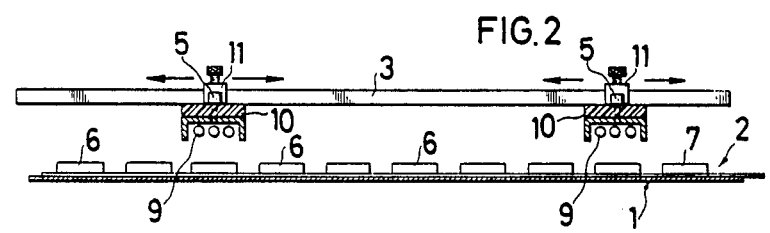
FIG. 2 shows the section II—II of FIG. 1.
Figure 1:
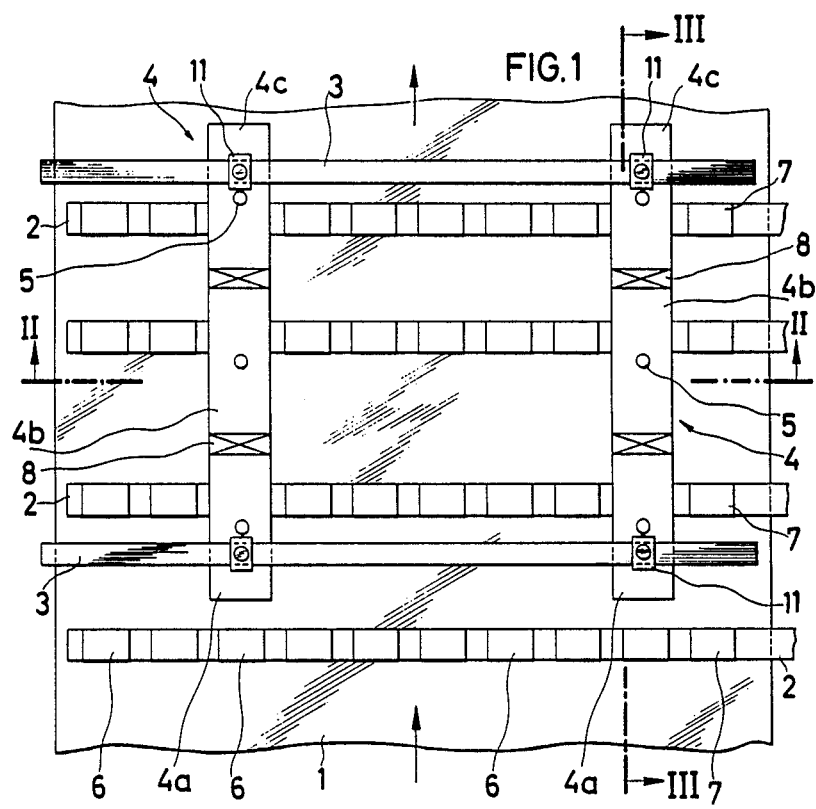
FIG. 1 shows a part of the transport apparatus in plan view.
Figure 3:
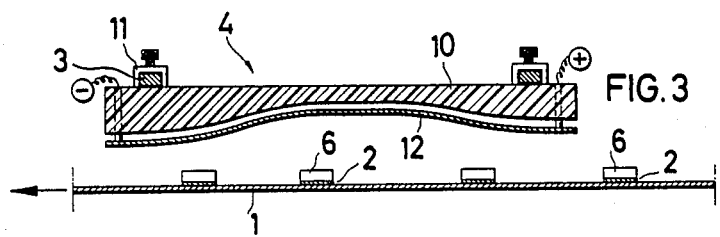
FIG. 3 shows the section III—III of FIG. 1, but with a band heater as heating device.

The test strip 2 laid on the conveyor belt 1 and having nine test zones 6 and one color compensation zone 7 is transported step by step underneath the measuring head of the ten-channel photometer (not shown). Above the conveyor belt and transverse to the direction of movement, which is indicated by arrows, a retaining device 3 is provided, on which at least one heating device 4 is displaceably arranged. The heating device 4 may consist of a plurality of heat radiators 4a, 4b, 4c, which are arranged one behind the other in the direction of movement of the conveyor belt 1. The individual heat radiators with the heating bars 9 are provided with a temperature controller 5 and are separated from one another by insulators 8 and from the retaining device 3 by insulators 10. 11 indicates the fastening of the heating device 4 to the retaining device 3. According to FIG. 3, the heating device 4 consists of a band heater 12, which extends in the direction of movement of the conveyor belt and has a varying distance from the latter.

I claim:

1. An apparatus for transporting test material in strip form underneath a measuring device, the test material having various test zones along the length of the strip, the apparatus comprising:
   conveyor means for transporting the test material;
   a retaining device disposed above the conveyor means at an angle transverse to the direction of movement of the conveyor means; and
   at least one heating device movably disposed on said retaining device for selectively heating individual test zones on the test material as the test material is transported by the conveyor means.

2. An apparatus as set forth in claim 1, wherein the heating device includes a plurality of heat radiators and temperature controllers for individually controlling each of said radiators, said radiators arranged in side-by-side relation to each other and substantially parallel to the direction of movement of the conveyor means.

3. An apparatus as set forth in claim 1, wherein between about one and nine heating devices are arranged on said retaining device.

4. An apparatus as set forth in claim 1, wherein said at least one heating device includes a band heater extending lengthwise in the direction of movement of said conveyor means, wherein said band heater is configured such that the spacing between said conveyor means and said band heater varies along the lengthwise dimension of said band heater.

* * * * *